US00PP10105P

United States Patent [19]

Wain

[11] Patent Number: Plant 10,105

[45] Date of Patent: Nov. 4, 1997

[54] CHRYSANTHEMUM PLANT NAMED 'HARVEST TIME'

[75] Inventor: Peter Wain, Hayling Island, United Kingdom

[73] Assignee: Cleangro Ltd., Chichester, United Kingdom

[21] Appl. No.: 317,022

[22] Filed: Oct. 3, 1994

[51] Int. Cl.[6] ..... A01H 5/00

[52] U.S. Cl. ..... Plt./82.2

[58] Field of Search ..... Plt./82.2

*Primary Examiner*—Howard J. Locker

*Attorney, Agent, or Firm*—C. A. Whealy

[57] ABSTRACT

A new and distinct cultivar of Chrysanthemum named Harvest Time characterized by its anemone-type inflorescences; bright yellow-colored ray florets; mature disc florets that are darker yellow than the ray floret color; flowering response of 56 days; large leaves; a freely branching and spreading plant habit; and good postproduction longevity with ray florets that do not fade and maintain good substance.

1 Drawing Sheet

BACKGROUND OF THE NEW PLANT

The present invention relates to a new and distinct cultivar of Chrysanthemum, botanically known as *Dendranthema grandiflora* and referred to by the cultivar name Harvest Time.

The new cultivar was developed by me in, Havant, Hampshire, United Kingdom, through controlled breeding by crossing the Chrysanthemum seedling selection P22-89 as the female parent with the Chrysanthemum seedling selection P6-89 as the male parent. The cultivar Harvest Time differs from its parent cultivars in leaf size, ray floret color, and plant vigor. Plants of selection P22-89 have larger leaves and the ray florets are lighter in color than plants of the cultivar Harvest Time. Plants of selection P6-89 have ray florets that are pink in color and are less vigorous than plants of the cultivar Harvest Time. Both selections were developed by me in Havant in a controlled breeding program and used only as breeding parents.

Asexual reproduction of the new cultivar by terminal cuttings taken by me in Havant has shown that the unique features of this new Chrysanthemum are stable and are reproduced true to type in successive generations.

The following characteristics have been repeatedly observed and are determined to be basic characteristics of Harvest Time, which in combination distinguish this Chrysanthemum from both its parent varieties and other cultivated Chrysanthemums of this type as a new and distinct cultivar:

1. Flat capitulum form.
2. Anemone-type inflorescences.
3. Ray florets that are bright yellow in color.
4. Mature disc florets that are darker yellow than mature ray florets.
5. Flowering response of 56 days from start of long nyctoperiods.
6. Large leaves that are 8.3 cm in length and 4.2 cm in width.
7. A freely branching and spreading plant habit.
8. Good postproduction longevity with ray florets that do not fade and maintain good substance.

Harvest Time is similar to the commercial Chrysanthemum cultivar Forge (U.S. Plant Pat. No. 7,470) in inflorescence form and ray floret color, however in side-by-side comparisons Harvest Time plants differ from plants of the cultivar Forge in the following characteristics:

1. Plant height: Plants of the cultivar Harvest Time are taller than plants of the cultivar Forge since plants of the cultivar Harvest Time have longer lateral branches compared to plants of the cultivar Forge.
2. Growth rate: Growth rate and vigor of plants of the cultivar Harvest Time is greater than growth rate and vigor of plants of the cultivar Forge.
3. Quantity of leaves: Plants of the cultivar Harvest Time have fewer leaves per lateral stem than plants of the cultivar Forge.
4. Leaf size: Plants of the cultivar Harvest Time have longer and broader leaves than plants of the cultivar Forge.
5. Inflorescence size: Inflorescences of the cultivar Harvest Time are larger in diameter than inflorescences of the cultivar Forge.
6. Quantity of ray florets: Inflorescences of the cultivar Harvest Time have fewer ray florets than inflorescences of the cultivar Forge.
7. Ray floret fading: Ray florets of inflorescences of the cultivar Harvest Time do not fade in color whereas ray florets of inflorescences of the cultivar Forge do fade.
8. Quantity of disc florets: Inflorescences of the cultivar Harvest Time have more disc florets than inflorescences of the cultivar Forge.
9. Disc floret color: Mature disc florets of inflorescences of the cultivar Harvest Time are darker than the ray florets. Mature disc florets of inflorescences of the cultivar Forge are the same color as the ray florets.

A detailed comparison of the differences between the cultivars Harvest Time and Forge appears in Chart A at the end of the specification.

DESCRIPTION OF THE PHOTOGRAPH

The accompanying colored photograph (FIG. 1) illustrates the overall appearance and inflorescence color of the new cultivar, showing the colors as true as it is reasonable possible to obtain in colored reproductions of this type. The photograph is a top view of a plant of the cultivar Harvest Time grown as a potted Chrysanthemum with five plants in a 16.5-cm clay pot.

DESCRIPTION OF THE NEW PLANT

The new cultivar has not been observed under all possible environmental conditions. The phenotype may vary significantly with variations in environment such as temperature, light intensity and daylength. The following observations and measurements describe plants grown in Oxnard, Calif., under commercial greenhouse conditions with average day temperatures ranging from 26° to 32° C. and average night temperatures ranging from 18° to 20° C. Color references are made to The Royal Horticultural Society Colour Chart except where general terms of ordinary dictionary significance are used. Numerical measurements represent averages of measurements taken on five plants.

Classification:

A. *Botanical.*—*Dendranthema grandiflora* cultivar Harvest Time.

B. *Common.*—Chrysanthemum.

C. *Commercial use.*—Potted plant.

Parentage:

*Female parent.*—Chrysanthemum seedling selection P22-89.

*Male parent.*—Chrysanthemum seedling selection P6-89.

Propagation:

A. *Type.*—Terminal tip cuttings.

B. *Time to initiate roots.*—7 to 10 days at soil temperatures of 22° C.

C. *Rooting habit.*—Fibrous and well-branched.

Plant description:

A. *General appearance.*—Perennial herbaceous flowering potted plant, upright and well-branched.

B. *Growth rate.*—Vigorous.

C. *Plant height.*—About 25 cm.

D. *Lateral branch length.*—About 18.9 cm.

E. *Quantity of lateral branches after removal of apical meristem.*—About 5.

F. *Stem color.*—147B.

G. *Foliage description.*—1. Number of leaves per lateral branch: about 13. 2. Leaf arrangement: Alternate. 3. Leaf shape and margin: Palmately lobed, pointed leaf apex and margin points. 4. Leaf size: a. Length: about 8.3 cm. b. Width: about 4.2 cm. 5. Leaf texture: Upper and under sides smooth and dull. Veins prominent on under side. Pubescence on both surfaces. 6. Young leaf color: a. Upper side: 147A. b. Under side: 147B. 7. Fully expanded leaf color: a. Upper side: 147A. b. Under side: 147B. 8. Petiole: a. Length: about 2 cm. b. Color: 147A. 9. Venation color: a. Upper side: 147B. b. Under side: 147B.

Flowering description:

A. *Inflorescence.*—Anemone-type inflorescence form. Florets arranged acropetally on a domed capitulum.

B. *Natural flowering season.*—Flowering occurs under lengthening nyctoperiods (at least 13 hours of darkness).

C. *Time to flower.*—Inflorescences are fully opened after 8 weeks of long nyctoperiods (15 hours of darkness).

D. *Quantity of inflorescences.*—After removal of the apical meristem, about 5 lateral breaks are formed per plant; each lateral stem develops about 6 inflorescences: usually about 30 inflorescences per plant.

E. *Ray florets.*— 1. Appearance: Satiny. 2. Texture: Glabrous, smooth. 3. Shape: Broad, oblanceolate with rounded apex. 4. Aspect: Slightly convex. 5. Margin: Entire. 6. Tip: Rounded. 7. Length: about 2.5 cm. 8. Width: about 1.1 cm. 9. Color: a. When opening, upper side: 14B. b. When opening, under side: 14C. c. Mature, upper side: 9A. d. Mature, under side: 9C. e. Fading to: 9A. 10. Number of ray florets per inflorescence: about 22. 11. Size of inflorescence: a. Diameter: about 5.9 cm. b. Height: about 1.5 cm.

F. *Disc florets.*— 1. Shape: Tubular. 2. Length: about 10 mm. 3. Width: about 3 mm. 4. Color: a. Immature: 154A. b. Mature: 14A. 5. Number of disc florets per inflorescence: about 197. 6. Diameter of disc: about 2.8 cm.

G. *Reproductive organs.*—*Androecium present on disc florets only and gynoecium present on both ray and disc florets. Anther color,* 2A, moderate pollen, 2A in color.

Disease resistance: No known Chrysanthemum diseases observed to date on plants grown under commercial greenhouse conditions.

Seed development: Development of seed on inflorescenes has not been observed.

CHART A

| Characteristic | Harvest Time | Forge |
|---|---|---|
| Plant height | 25 cm | 18 cm |
| Lateral branch length | 18.9 cm | 13.9 cm |
| Growth rate, vigor | high | low |
| Quantity of leaves per lateral branch | 13 | 15 |
| Leaf length | 8.3 cm | 5.6 cm |
| Leaf width | 4.2 cm | 3.6 cm |
| Inflorescence size (diameter) | 5.9 cm | 5.2 cm |
| Quantity of ray florets | 22 | 36 |
| Ray floret color, faded | 9A | 9B |
| Quantity of disc florets | 197 | 163 |
| Mature disc floret color | 14A | 9A |

I claim:

1. A new and distinct cultivar of Chrysanthemum plant named Harvest Time substantially as herein illustrated and described.

* * * * *

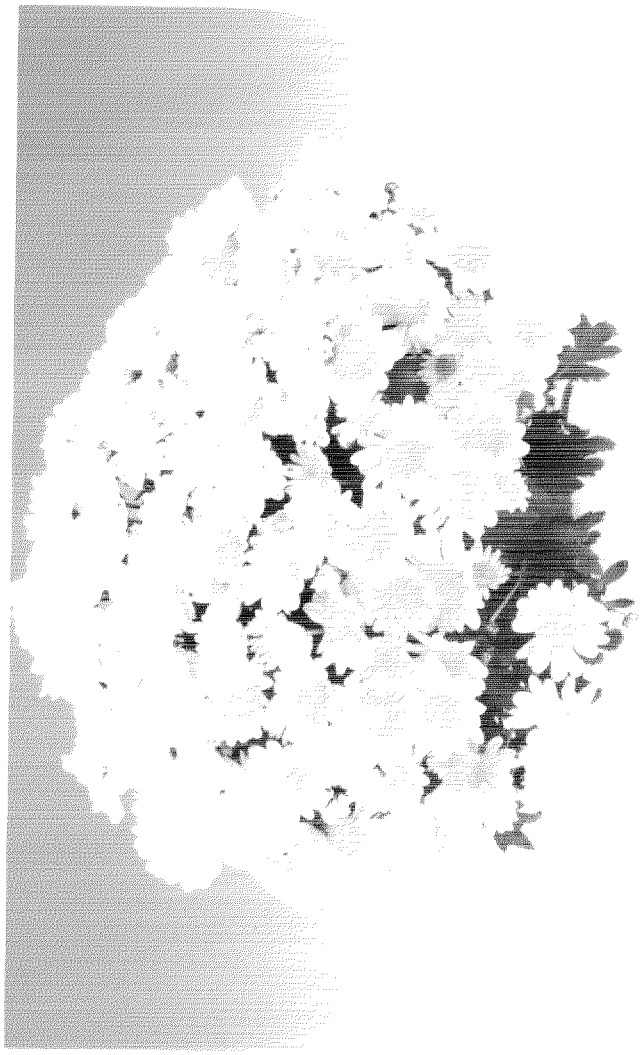
FIGURE 1. CHRYSANTHEMUM PLANT NAMED HARVEST TIME